US012703670B2

(12) United States Patent
Pacheco et al.

(10) Patent No.: US 12,703,670 B2
(45) Date of Patent: Aug. 11, 2026

(54) METHOD FOR PURIFYING A FEEDSTOCK RESULTING FROM A METHOD FOR DEPOLYMERIZING STYRENE COMPOUNDS

(71) Applicant: COMPAGNIE GENERALE DES ETABLISSEMENTS MICHELIN, Clermont-Ferrand (FR)

(72) Inventors: Nuno Pacheco, Clermont-Ferrand (FR); Pierre Kiener, Clermont-Ferrand (FR); Pierre Sere-Peyrigain, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 168 days.

(21) Appl. No.: 18/691,202

(22) PCT Filed: Sep. 8, 2022

(86) PCT No.: PCT/FR2022/051700
§ 371 (c)(1),
(2) Date: Mar. 12, 2024

(87) PCT Pub. No.: WO2023/041862
PCT Pub. Date: Mar. 23, 2023

(65) Prior Publication Data

US 2024/0376027 A1 Nov. 14, 2024

(30) Foreign Application Priority Data

Sep. 16, 2021 (FR) ...................................... 2109745

(51) Int. Cl.
*C07C 7/04* (2006.01)
*B01D 3/14* (2006.01)
(Continued)

(52) U.S. Cl.
CPC ................ *C07C 7/04* (2013.01); *B01D 3/141* (2013.01); *B01D 3/143* (2013.01); *B01D 3/34* (2013.01); *C07C 7/005* (2013.01)

(58) Field of Classification Search
CPC ....... C07C 7/04–05; C07C 7/005; C07C 7/20; B01D 3/141; B01D 3/143; B01D 3/34
See application file for complete search history.

(56) References Cited

U.S. PATENT DOCUMENTS 2,457,361 A 12/1948 Gadwa
3,904,484 A * 9/1975 King ......................... C07C 7/05 203/52
(Continued)

FOREIGN PATENT DOCUMENTS

WO 2014/098816 A1 6/2014
WO 2020/144165 A1 7/2020

OTHER PUBLICATIONS

International Search Report dated Jan. 3, 2023, in corresponding PCT/FR2022/051700 (4 pages).

*Primary Examiner* — Renee Robinson
(74) *Attorney, Agent, or Firm* — VENABLE LLP

(57) ABSTRACT

A process for the purification of a feedstock resulting from a process for the depolymerization of styrene compounds, referred to as feedstock of the purification process, comprises at least a separation step producing an extract rich in light compounds, a raffinate rich in heavy compounds and a stream rich in styrene, and a step of separation of the stream rich in styrene into at least a stream comprising predominantly ethylbenzene, a stream comprising predominantly styrene and a stream of heavy compounds.

12 Claims, 2 Drawing Sheets

(51) Int. Cl.
*B01D 3/34* (2006.01)
*C07C 7/00* (2006.01)

(56) References Cited

U.S. PATENT DOCUMENTS

| | | | | |
|---|---|---|---|---|
| 4,033,829 | A * | 7/1977 | Higgins, Jr. | C07C 7/20 203/29 |
| 4,113,787 | A * | 9/1978 | Ward | C07C 5/32 585/441 |
| 4,628,136 | A * | 12/1986 | Sardina | C07C 15/46 585/440 |
| 6,171,449 | B1 * | 1/2001 | Welch | B01D 3/146 203/1 |
| 9,902,667 | B2 | 2/2018 | Welch | |
| 11,999,686 | B2 | 6/2024 | Niessner et al. | |
| 2015/0336859 | A1 | 11/2015 | Welch | |
| 2022/0081372 | A1 | 3/2022 | Niessner et al. | |

* cited by examiner

[Fig 1]
PRIOR ART
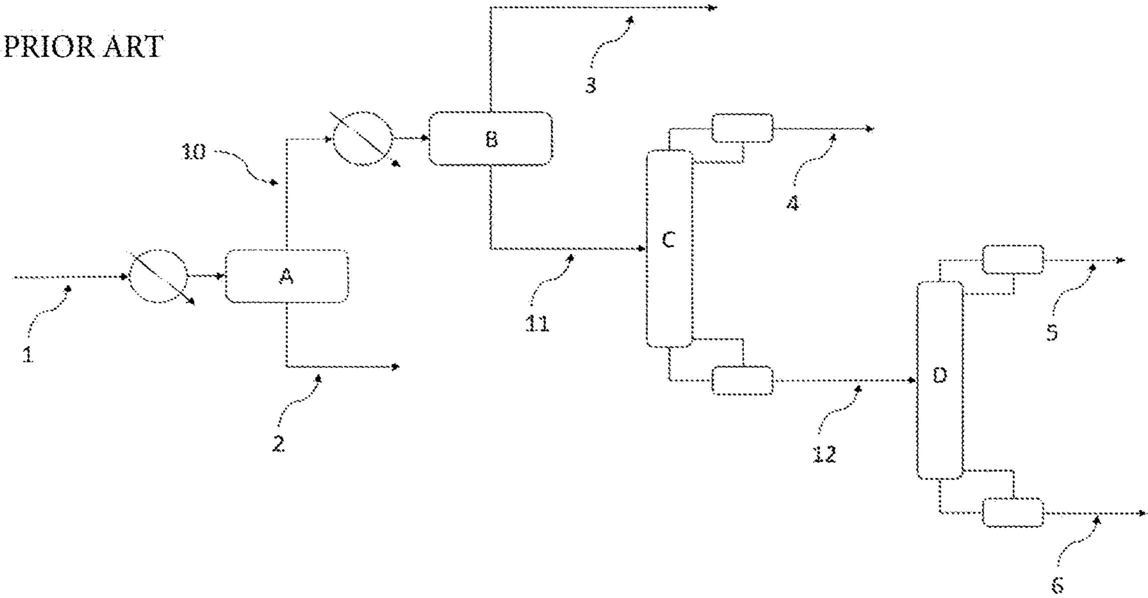
[Fig 2]
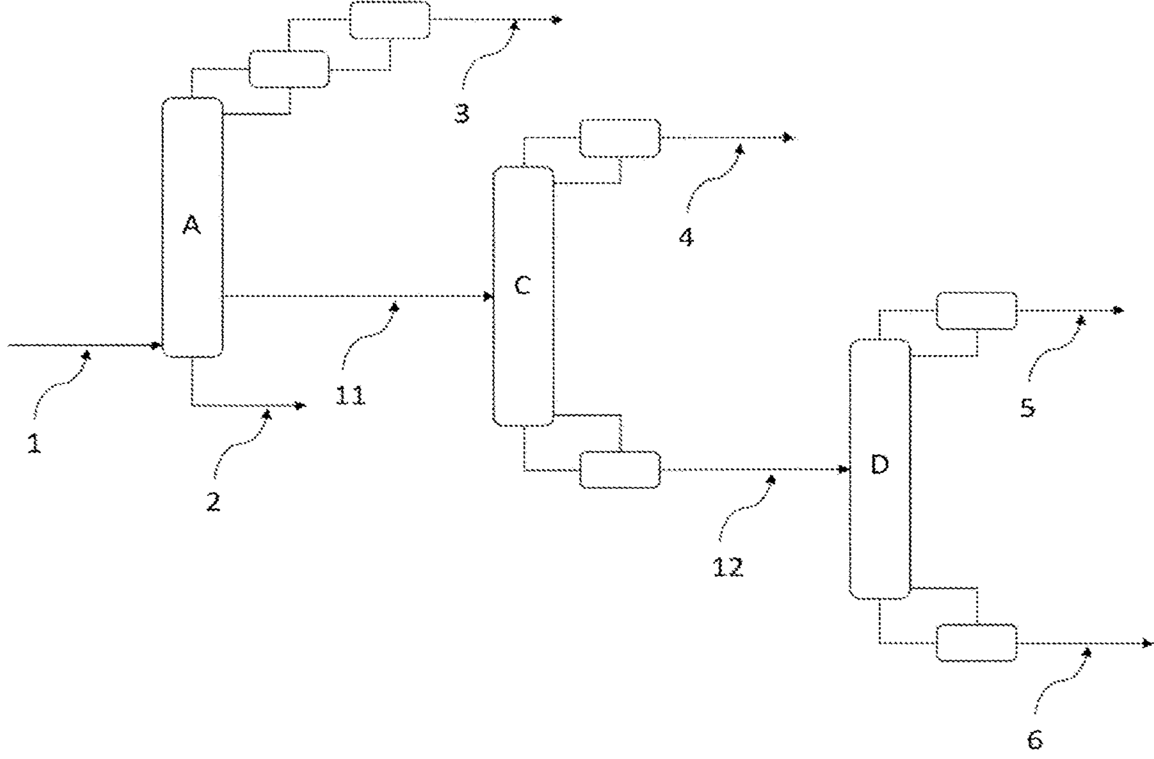

[Fig 3]
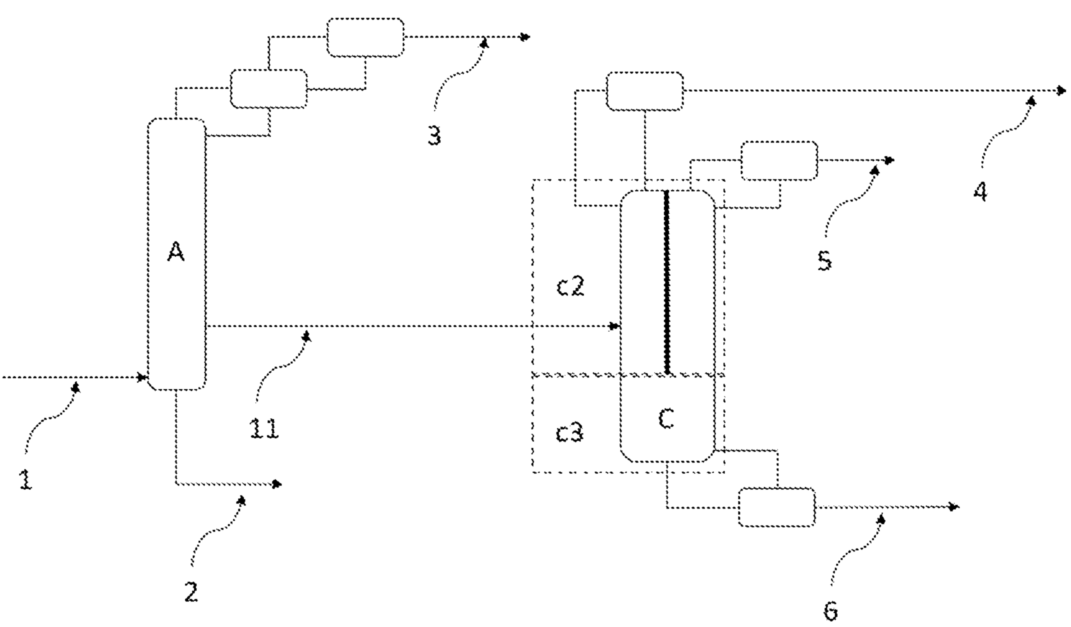
[Fig 4]
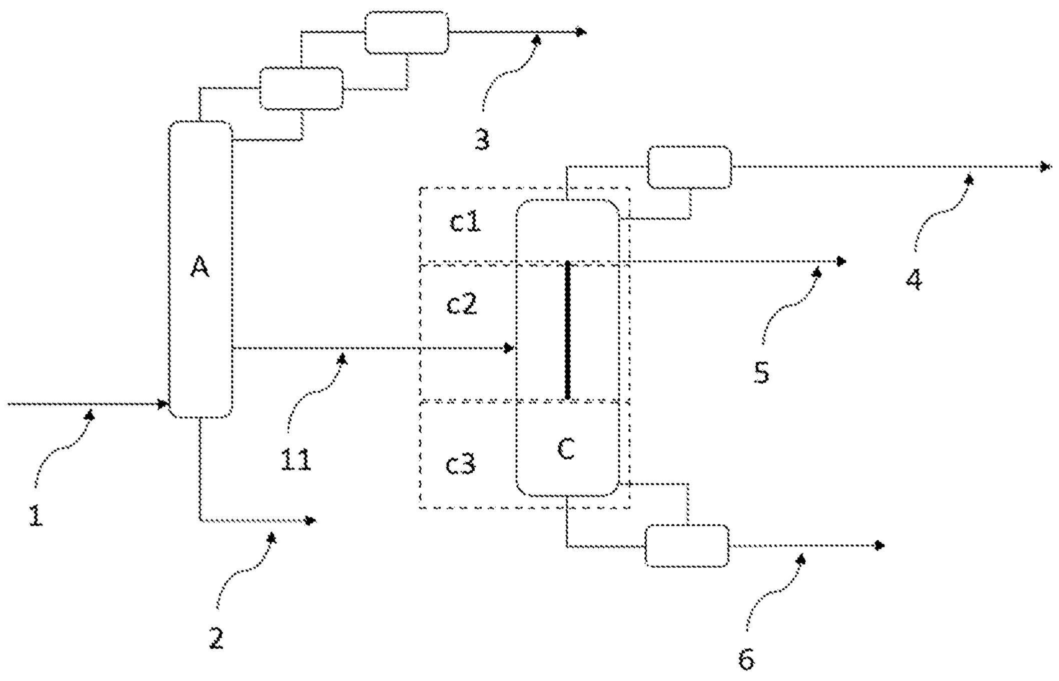

METHOD FOR PURIFYING A FEEDSTOCK RESULTING FROM A METHOD FOR DEPOLYMERIZING STYRENE COMPOUNDS

TECHNICAL FIELD OF THE INVENTION

The present invention relates to the field of processes for the separation of styrene.

BACKGROUND

Styrene is a monomer very widely used in industry, whether for example for the production of polystyrene, which has multiple fields of application, or the production of elastomers, such as styrene-butadiene rubber (SBR). It can be obtained in many ways, the main one being by the dehydrogenation of ethylbenzene, or to a lesser extent by the oxidation of ethylbenzene, followed by the reaction with propylene and then the dehydration of the product obtained.

With a view to reducing the pressure on fossil resources, recent developments have focused on the depolymerization of styrene compounds.

Whatever the method used, the styrene produced must be purified in order to meet the specifications required by polymerization processes. The required purities, typically more than 99.8% by weight of styrene, result in the use of separation processes which are sizeable, in terms of number of steps and of energy consumption.

The document U.S. Pat. No. 2,457,361 describes a process which makes it possible to separate styrene from a feedstock resulting from the production of styrene by dehydrogenation of ethylbenzene, by separating, in a first step, benzene and toluene, then the compounds heavier than styrene, and finally ethylbenzene by a sequence of seven distillation columns, the majority of which are operated under vacuum in order to limit the exposure to the temperature of the styrene. This complex sequence is mainly the consequence of the high ethylbenzene content of the feedstock to be treated.

The feedstocks resulting from processes for the depolymerization of styrene compounds exhibit lower ethylbenzene contents than the "conventional" processes in which styrene is a reaction product of ethylbenzene. However, these feedstocks comprise a greater content of "heavy" compounds, that is to say compounds, the boiling point of which is higher than that of styrene, and need to be cooled rapidly in order to avoid polymerization of styrene.

The document WO 2020/144165 describes the separation of styrene from a feedstock resulting from the pyrolysis of styrene residues by, in a first step, separating the heavy compounds, then separating the ethylbenzene and finally separating the polymerization-inhibiting compounds. The feedstock is cooled rapidly at the feed tray of the first distillation column. This document teaches that the "heavy" compounds are particularly viscous and need to be separated early in the process for the purification of styrene. These characteristics of the heavy compounds require a particular design of the separation plates of the distillation columns and of their reboilers.

On continuing its research studies, the applicant company has discovered a sequence of steps making it possible to treat a feedstock resulting from a process for the depolymerization of styrene compounds in order to obtain a stream comprising predominantly styrene with the specifications necessary to feed a polymerization process, with in particular very low contents of "heavy" compounds, including, for example, α-methylstyrene.

SUMMARY

The invention relates to a process for the purification of a feedstock resulting from a process for the depolymerization of styrene compounds, referred to as feedstock of the purification process, comprising at least the following steps:

a. a separation step employing a distillation column fed at the column bottom with the feedstock of the purification process and producing, at the column top, an extract rich in light compounds, at the bottom a raffinate rich in heavy compounds and, by a sidestream withdrawal, a stream rich in styrene, said column having as sole heat supply said feedstock of the purification process:

b. a step of separation of the stream rich in styrene into at least a stream comprising predominantly ethylbenzene, a stream comprising predominantly styrene and a stream of heavy compounds.

BRIEF DESCRIPTION OF THE FIGURES

FIG. 1 is a diagrammatic representation of a separation process according to the prior art.

FIG. 2 is a diagrammatic representation of a first preferred arrangement of the process according to the invention.

FIG. 3 is a diagrammatic representation of an alternative form of a second preferred arrangement of the process according to the invention.

FIG. 4 is a diagrammatic representation of another alternative form of a second preferred arrangement of the process according to the invention.

DEFINITIONS

The compounds comprising carbon which are mentioned in the description can be of fossil origin or be biobased. In the latter case, they may partially or completely result from biomass or may be obtained from renewable starting materials resulting from biomass. Polymers, plasticizers, fillers, and the like, are concerned in particular.

The purification of the feedstocks resulting from processes for the depolymerization of styrene compounds requires taking into account the specificities of these feedstocks, and in particular a content of "heavy" compounds, that is to say compounds, the boiling point of which is higher than that of styrene, which is greater than in feedstocks resulting from processes for the production of styrene by dehydrogenation of ethylbenzene, and a much lower ethylbenzene content. The purification strategies developed to treat the feedstocks resulting from these dehydrogenation processes are thus not suitable for the purification of feedstocks resulting from processes for the depolymerization of styrene compounds.

Feedstock of the Purification Process

A subject matter of the invention is a process for the purification of a feedstock resulting from a process for the depolymerization of styrene compounds. The term "resulting from a process for the depolymerization of styrene compounds" is understood to mean that the feedstock results from a process producing styrene from styrene-comprising compounds, such as polystyrene or styrene elastomers. Such processes are known to a person skilled in the art and can, for example, be a pyrolysis process or an enzymatic decomposition process.

Preferably, the feedstock of the process according to the invention results from a pyrolysis process.

The feedstock of the process according to the invention comprises predominantly styrene, that is to say at least 50% by weight of styrene, preferentially at least 60% by weight of styrene.

Preferably, the feedstock of the purification process comprises at most 10% by weight of ethylbenzene, preferably at most 5% by weight of ethylbenzene and in a preferred way at most 3% by weight of ethylbenzene.

Preferentially, the feedstock of the purification process comprises at least 10% by weight of compounds, the boiling point of which is greater than that of styrene.

These contents of ethylbenzene and of "heavy" compounds clearly distinguish a feedstock as treated in the process according to the invention from a feedstock resulting from a process for the production of styrene from ethylbenzene.

Step a) of Separation of a Feedstock Resulting from a Process for the Depolymerization of Styrene Compounds The process according to the invention comprises a separation step employing a distillation column fed at the column bottom with the feedstock of the purification process and producing, at the column top, an extract rich in light compounds, at the bottom a raffinate rich in heavy compounds and, by a sidestream withdrawal, a stream rich in styrene, said column having as sole heat supply said feedstock of the purification process.

The feedstock of the purification process is at high temperature, preferably at a temperature greater than 300° C., preferentially at a temperature of between 300° C. and 400° C. This temperature is sufficient for the column not to require another heat supply. Preferably, the process for the depolymerization of styrene compounds is a pyrolysis process and the feedstock resulting from the pyrolysis reactor directly feeds the process of the invention, without intermediate cooling, heating or separation operation.

By feeding the feedstock at the column bottom, the feedstock is rapidly cooled, thus making it possible to limit possible polymerization reactions of the styrene. This feeding additionally makes possible better management of the "heavy" compounds. This is because the absence of a recirculation system at the column bottom, generally used for the temperature maintenance of the distillation column, greatly limits the risks of fouling by the "heavy" compounds, which are particularly viscous.

A raffinate rich in heavy compounds is withdrawn at the column bottom.

At the column top, the vapour effluent is cooled to a temperature of between 30° C. and 50° C., preferably of between 35° C. and 45° C. The condensed liquid fraction is returned at the column top as reflux, while the vapour fraction is subsequently subcooled to a temperature of between −5° C. and 10° C., preferentially between −5° C. and 5° C., in order to condense the styrene possibly entrained with the light compounds. The stream condensed after subcooling is returned at the column top as reflux. The residual vapour fraction constitutes the extract rich in light compounds. This extract can subsequently be upgraded, for example in energy form. A first cooling makes possible maximum use of cooling water at ambient temperature as cold utility and minimizes the use of specific cold utility to obtain subcooling, which favourably impacts the life cycle analysis of the process according to the invention.

The distillation column employed in step a) of the process according to the invention comprises from 5 to 20 theoretical stages, preferably at most 15 theoretical stages, in a preferred way from 8 to 12 theoretical stages.

A stream rich in styrene is withdrawn on an intermediate plate. This withdrawal plate is located in the lower third of the distillation column, preferably from 1 to 3 theoretical stages from the bottom plate. This withdrawal at a low position of the column, slightly away from the bottom plate, makes it possible to limit the entrainment of heavy compounds in the stream rich in styrene and correspondingly limits the risks of fouling of the subsequent items of equipment.

The distillation column employed in step a) of the process according to the invention is operated at a pressure of between 0.1 and 2.0 bara, preferably between 0.5 and 1.5 bara and in a preferred way between 0.5 and 1.1 bar, the operating pressure being understood as the pressure measured at the column top. The term "bara" is understood to mean bar absolute, as opposed to a pressure expressed in bar relative, commonly denoted "barg" according to the notation "bar gauge".

Step a) of the process according to the invention makes it possible to limit the polymerization of styrene, with in particular rapid cooling of the feedstock of the process by the feeding of this feedstock at the column bottom. Preferably, and in order to limit even more the risk of polymerization, an inhibitor of the polymerization of styrene to give polystyrene, such as 2,2,6,6-tetramethyl-4-oxopiperidinooxy, can be fed into the distillation column of step a) of the process, preferably at the column top.

Step b) of Separation of the Stream Rich in Styrene

In a step b), the stream rich in styrene resulting from step a) of the process is separated into at least a stream comprising predominantly ethylbenzene, a stream comprising predominantly styrene and a stream of heavy compounds.

The separation step b) makes it possible to obtain a stream comprising predominantly styrene which can feed a process for the polymerization of styrene, thus meeting the specifications of such processes, with in particular a very high content of styrene, preferably of greater than 99.5% by weight, and contents of compounds, such as ethylbenzene, benzene, cumene, α-methylstyrene and oligomers of styrene, which are very low.

In a first preferred arrangement, step b) of separation of the stream rich in styrene comprises two successive separation sections.

A first separation section is fed with the stream rich in styrene resulting from step a) and makes it possible to separate a stream comprising predominantly ethylbenzene and a styrenic raffinate.

This first section is carried out in a distillation column comprising from 60 to 100 theoretical stages, and is operated at a pressure of less than or equal to 0.25 bara at the column top so as to maintain the temperature at the column bottom at a value of less than or equal to 120° C. The distillation column of the first section is fed with the stream rich in styrene resulting from step a) at the bottom of the upper third of the column. For example, for a column comprising 60 theoretical stages, the stream rich in styrene is fed to a stage between the $18^{th}$ theoretical stage and the $22^{nd}$ theoretical stage, the stages being numbered from the top downwards.

The reflux ratio at the condenser of this column, corresponding to the flow rate by weight of reflux fed at the column top to the flow rate by weight of stream comprising predominantly ethylbenzene, is preferentially of between 60 and 300. This parameter varies greatly as a function of the ethylbenzene content of the stream rich in styrene. The lower the ethylbenzene content of the stream rich in styrene, the higher the reflux ratio at the condenser of the column.

The reflux ratio at the reboiler of this column, corresponding to the flow rate by weight of reflux fed at the column bottom to the flow rate by weight of styrenic raffinate, is preferentially of between 4 and 10, preferably of between 5 and 9.

A second separation section is fed with the styrenic raffinate resulting from the first separation section and produces a stream comprising predominantly styrene and a stream of heavy compounds.

This second section is carried out in a distillation column comprising from 40 to 100 theoretical stages, preferably comprising from 40 to 70 theoretical stages, and is operated at a pressure of less than or equal to 0.25 bara at the column top so as to maintain the temperature at the column bottom at a value of less than or equal to 120° C.

The distillation column of the first section is fed with the styrenic raffinate resulting from the first separation section in the lower part of the column, preferentially in the top of the lower fifth of the column. For example, for a column comprising 50 theoretical stages, the styrenic raffinate resulting from the first separation section is fed to a stage between the $35^{th}$ theoretical stage and the $45^{th}$ theoretical stage, the stages being numbered from the top downwards.

The reflux ratio at the condenser of this column, corresponding to the flow rate by weight of reflux fed at the column top to the flow rate by weight of stream comprising predominantly styrene, is preferentially of between 4 and 8.

The reflux ratio at the reboiler of this column, corresponding to the flow rate by weight of reflux fed at the column bottom to the flow rate by weight of stream of heavy compounds, is preferentially of between 40 and 200, this ratio being greatly influenced by the content of compounds such as cumene and α-methylstyrene.

In another preferred arrangement, step b) of separation of the stream rich in styrene is carried out in a divided wall distillation column.

A divided wall column is an item of distillation equipment well known to a person skilled in the art in which an internal wall leaktight to fluids and arranged vertically separates a part of the column into two distinct zones. A divided wall column thus generally consists of a lower common part in which the separation stages are not divided by the internal wall, of a divided part in which the separation stages are divided by the internal wall and of an upper common part in which the separation stages are not divided by the internal wall.

The divided wall column comprises, in total, from 70 to 130 theoretical stages, preferentially from 80 to 120 theoretical stages, very preferentially from 90 to 110 theoretical stages. The internal wall is preferentially centred, that is to say that it partitions the column in the length where it is present into two parts of equal volume. When the number of theoretical stages on either side of the internal wall is different, for example because of the use of types of distributor plates or of packing which are different, the total number of theoretical stages of the column is understood as the sum of the theoretical stages of the common parts and of the greater number of stages between the two divided parts. The column is operated at a pressure of less than or equal to 0.25 bara at the column top so as to maintain the temperature at the column bottom at a value of less than or equal to 120° C.

The stream rich in styrene resulting from step a) of the process is fed on one side of the internal wall on a stage ranging from the $10^{th}$ to the $20^{th}$ theoretical stage, preferably ranging from the $12^{th}$ to the $18^{th}$ theoretical stage and very preferentially to the $15^{th}$ theoretical stage, the stages being numbered from the top downwards.

In a first alternative form of this arrangement, the lower common part of the divided wall column comprises from 8 to 12 theoretical stages and the upper common part comprises from 8 to 12 theoretical stages. The stream comprising predominantly styrene is withdrawn, with respect to the internal wall, in the opposite part to the part where the stream rich in styrene is injected. The withdrawal is carried out on a stage close to the upper part of the divided part, preferentially on one of the 5 upper stages of the divided part, preferably on one of the 3 upper stages of the divided part, very preferably on one of the two upper stages of the divided part and very preferentially on the first stage of the divided part, counting the stages from the top.

The stream comprising predominantly ethylbenzene is withdrawn at the column top and the stream of heavy compounds is withdrawn at the column bottom.

The reflux ratio at the condenser of this column, corresponding to the flow rate by weight of reflux fed at the column top to the flow rate by weight of stream comprising predominantly ethylbenzene, is preferentially of between 60 and 300. This parameter varies greatly as a function of the ethylbenzene content of the stream rich in styrene. The lower the ethylbenzene content of the stream rich in styrene, the higher the reflux ratio at the condenser of the column.

The reflux ratio at the reboiler of this column, corresponding to the flow rate by weight of reflux fed at the column bottom to the flow rate by weight of stream of heavy compounds, is preferentially of between 50 and 200, this ratio being greatly influenced by the content of compounds such as cumene and α-methylstyrene.

In a second alternative form of this arrangement, the divided wall column does not comprise an upper common part, that is to say that the wall extends up to the top of the divided wall column.

In this alternative form, the lower common part comprises from 2 to 12 theoretical stages, preferentially from 2 to 10 theoretical stages and very preferentially from 2 to 4 theoretical stages.

In this alternative form, the divided wall column preferentially comprises, in total, from 60 to 80 theoretical stages.

In this alternative form, the stream comprising predominantly styrene is withdrawn, with respect to the internal wall, in the opposite part to the part where the stream rich in styrene is injected. The withdrawal is carried out at the column top.

The stream comprising predominantly ethylbenzene is withdrawn at the column top in the same part as the part where the stream rich in styrene is injected.

The reflux ratio at the condenser of this column for the divided part located on the side of the feeding with stream rich in styrene, corresponding to the flow rate by weight of reflux fed at the column top in this part to the flow rate by weight of stream comprising predominantly ethylbenzene, is preferentially of between 60 and 300. This parameter varies greatly as a function of the ethylbenzene content of the stream rich in styrene. The lower the ethylbenzene content of the stream rich in styrene, the higher the reflux ratio at the condenser of the column.

The reflux ratio at the condenser of this column for the divided part located on the side of the withdrawal of the stream comprising predominantly styrene, corresponding to the flow rate by weight of reflux fed at the column top to the flow rate by weight of stream comprising predominantly styrene, is preferentially of between 1 and 10.

The reflux ratio at the reboiler of this column, corresponding to the flow rate by weight of reflux fed at the column bottom to the flow rate by weight of stream of heavy compounds, is preferentially of between 60 and 200, this ratio being greatly influenced by the content of compounds such as cumene and α-methylstyrene.

Preferably, and in order to limit even more the risk of polymerization, an inhibitor of the polymerization of styrene to give polystyrene, such as 2,2,6,6-tetramethyl-4-oxopiperidinooxy, can be fed into the column(s) employed in the separation step b), preferentially at the top of the column(s) employed in the separation stage b).

EXAMPLES

Example 1

FIG. 1 is a diagrammatic representation of a separation process according to the prior art.

A feedstock of the purification process (1) feeds, after having been cooled to a temperature of 209° C., a first separation step (A), operated at a pressure of 1.1 bara, which separates this feedstock into a raffinate rich in heavy compounds (2) withdrawn at the column bottom and a light cut (10) withdrawn at the column top.

This light cut (10) is cooled to a temperature of 40° C. and feeds a second separation step (B), operated at a pressure of 1.1 bara, which produces, at the top, an extract rich in light compounds (3) and, at the bottom, a stream rich in styrene (11). The latter feeds a distillation column (C) comprising, while including condenser and reboiler, 60 theoretical stages and operated at a top pressure of 0.25 bara, which produces, at the top, a stream comprising predominantly ethylbenzene (4) and, at the bottom, a styrenic raffinate (12). The stream rich in styrene (11) is fed at the level of the 20$^{th}$ theoretical stage, the stages being numbered starting from the condenser. The temperature is 76° C. at the condenser and 101° C. at the reboiler. The reflux ratio at the column top, corresponding to the reflux flow rate divided by the flow rate of stream comprising predominantly ethylbenzene (4) (by weight), is equal to 88. The reflux ratio at the column bottom, corresponding to the reflux flow rate divided by the flow rate of styrenic raffinate (12) (by weight), is equal to 7.

The styrenic raffinate (12) feeds a distillation column (D) comprising, while including the condenser and reboiler, 50 theoretical stages and operated at a top pressure of 0.25 bara, which produces, at the top, a stream comprising predominantly styrene (5) and, at the bottom, a stream of heavy compounds (6). The styrenic raffinate (12) is fed at the level of the 40$^{th}$ theoretical stage, the stages being numbered starting from the condenser. The temperature is 99° C. at the condenser and 128° C. at the reboiler. The reflux ratio at the column top, corresponding to the reflux flow rate divided by the flow rate of stream comprising predominantly styrene (5) (by weight), is equal to 6. The reflux ratio at the column bottom, corresponding to the reflux flow rate divided by the flow rate of stream of heavy compounds (6) (by weight), is equal to 48.

Example 2

FIG. 2 is a diagrammatic representation of a first preferred arrangement of the process according to the invention.

A feedstock of the purification process (1) feeds, at the column bottom, a first distillation column (A) comprising, while including condenser and reboiler, 10 theoretical stages and operated at a top pressure of 1 bara, which separates this feedstock into a raffinate rich in heavy compounds (2) withdrawn at the column bottom, an extract rich in light compounds (3) withdrawn at the top and a stream rich in styrene (11) produced by a sidestream withdrawal, withdrawn at the level of the 7$^{th}$ theoretical stage. The vapour effluent at the column top is cooled a first time to 40° C. the condensed liquid fraction being returned at the column top, then subcooled to 2° C. in order to condense the styrene entrained with the vapour effluent. The condensed liquid fraction after subcooling is returned at the column top with the liquid fraction resulting from the first cooling. The residual vapour fraction constitutes the extract rich in light compounds (3). The column (A) has, as sole heat supply, that provided by the feedstock of the purification process (1).

The stream rich in styrene (11) feeds a distillation column (C) comprising, while including condenser and reboiler, 60 theoretical stages and operated at a top pressure of 0.25 bara, which produces, at the top, a stream comprising predominantly ethylbenzene (4) and, at the bottom, a styrenic raffinate (12). The stream rich in styrene (11) is fed at the level of the 20$^{th}$ theoretical stage, the stages being numbered starting from the condenser. The temperature is 88° C. at the condenser and 105° C. at the reboiler. The reflux ratio at the column top, corresponding to the reflux flow rate divided by the flow rate of stream comprising predominantly ethylbenzene (4) (by weight), is equal to 243. The reflux ratio at the column bottom, corresponding to the reflux flow rate divided by the flow rate of styrenic raffinate (12) (by weight), is equal to 7.

The styrenic raffinate (12) feeds a distillation column (D) comprising, while including the condenser and reboiler, 50 theoretical stages and operated at a top pressure of 0.25 bara, which produces, at the top, a stream comprising predominantly styrene (5) and, at the bottom, a stream of heavy compounds (6). The styrenic raffinate (12) is fed at the level of the 40$^{th}$ theoretical stage, the stages being numbered starting from the condenser. The temperature is 99° C. at the condenser and 125° C. at the reboiler. The reflux ratio at the column top, corresponding to the reflux flow rate divided by the flow rate of stream comprising predominantly styrene (5) (by weight), is equal to 7. The reflux ratio at the column bottom, corresponding to the reflux flow rate divided by the flow rate of stream of heavy compounds (6) (by weight), is equal to 89.

Example 3

FIG. 3 is a diagrammatic representation of an alternative form of a second preferred arrangement of the process according to the invention.

A feedstock of the purification process (1) feeds, at the column bottom, a first distillation column (A) comprising, while including condenser and reboiler, 10 theoretical stages and operated at a top pressure of 1 bara, which separates this feedstock into a raffinate rich in heavy compounds (2) withdrawn at the column bottom, an extract rich in light compounds (3) withdrawn at the top and a stream rich in styrene (11) produced by a sidestream withdrawal, withdrawn at the level of the 7$^{th}$ theoretical stage. The vapour effluent at the column top is cooled a first time to 40° C., the condensed liquid fraction being returned at the column top, then subcooled to 2° C. in order to condense the styrene entrained with the vapour effluent. The condensed liquid fraction after subcooling is returned at the column top with the liquid fraction resulting from the first cooling. The residual vapour fraction constitutes the extract rich in light compounds (3). The column (A) has, as sole heat supply, that provided by the feedstock of the purification process (1).

The stream rich in styrene (11) feeds a divided wall column (C) which produces, at the top of the part where the stream rich in styrene (11) is injected, a stream comprising predominantly ethylbenzene (4) and, at the top of the opposite part, with respect to the internal wall, to the part where the stream rich in styrene (11) is injected, a stream comprising predominantly styrene (5). This column (C) also produces, at the bottom, a stream of heavy compounds (6).

The divided wall column (C) comprises two zones: a divided part (c2) comprising 67 theoretical stages in which the internal wall, extending vertically, divides the column into two zones between which the fluids do not flow, the internal wall extending up to the column top, and a lower common part (c3) comprising 3 theoretical stages. The stream rich in styrene (11) feeds the divided wall column (C) at the level of the 20$^{th}$ theoretical stage.

The temperature of the condenser on the side of the withdrawal of the stream comprising predominately styrene (5) is 99° C. The reflux ratio at the column top for this part, corresponding to the reflux flow rate divided by the flow rate of stream comprising predominantly styrene (5) (by weight), is equal to 6.

The temperature of the condenser on the side of the withdrawal of the stream comprising predominately ethylbenzene (4) is 84° C. The reflux ratio at the column top for this part, corresponding to the reflux flow rate divided by the flow rate of stream comprising predominantly ethylbenzene (4) (by weight), is equal to 112.

The reflux ratio at the column bottom, corresponding to the reflux flow rate divided by the flow rate of stream of heavy compounds (6) (by weight), is equal to 226. The temperature at the reboiler is 117° C.

Table 1 shows the performance qualities of these different processes in terms of consumption of hot utilities (making it possible to heat the streams), of cold utilities (making it possible to cool the streams), of purity of the styrene produced and of styrene yield, defined as the ratio of the flow rate of pure styrene in the stream comprising predominantly styrene (5) to the flow rate of pure styrene in the feedstock of the purification process (1).

The consumptions of hot and cold utilities are expressed in base 100, on the basis of the consumptions of the process illustrated by FIG. 1. A value of greater than 100 shows a higher consumption.

TABLE 1

| | Example 1 | Example 2 | Example 3 |
|---|---|---|---|
| Cold utility consumption | 100 | 102 | 93 |
| Hot utility consumption | 100 | 103 | 89 |
| Styrene purity | 99.98% | 99.98% | 99.97% |
| Styrene recovery | 96.8% | 95.5% | 97.1% |

It is observed that the process of Example 2 makes it possible, with similar performance qualities to the process of Example 1, to significantly limit the problems of fouling of the exchangers and of the items of equipment in the first steps of the purification, with limited risks of stoppage and thus a more regular production, which has a positive impact on the overall life cycle analysis of the process.

The process of Example 3, besides the limitation of the problems of fouling, makes it possible in addition to improve the styrene recovery for a lower energy consumption, with a further enhanced impact on the life cycle analysis of the process.

FIG. 4 is a diagrammatic representation of another alternative form of a second preferred arrangement of the process according to the invention.

A feedstock of the purification process (1) feeds, at the column bottom, a first distillation column (A) comprising, while including condenser and reboiler, 10 theoretical stages and operated at a top pressure of 1 bara, which separates this feedstock into a raffinate rich in heavy compounds (2) withdrawn at the column bottom, an extract rich in light compounds (3) withdrawn at the top and a stream rich in styrene (11) produced by a sidestream withdrawal. The vapour effluent at the column top is cooled a first time to 40° C., the condensed liquid fraction being returned at the column top, then subcooled to 2° C. in order to condense the styrene entrained with the vapour effluent. The condensed liquid fraction after subcooling is returned at the column top with the liquid fraction resulting from the first cooling. The residual vapour fraction constitutes the extract rich in light compounds (3). The column (A) has, as sole heat supply, that provided by the feedstock of the purification process (1).

The stream rich in styrene (11) feeds a divided wall column (C) which produces, at the top, a stream comprising predominantly ethylbenzene (4), by a sidestream withdrawal a stream comprising predominantly styrene (5) and, at the bottom, a stream of heavy compounds (6).

The divided wall column (C) comprises three zones: an upper common part (c1), a divided part (c2) in which the internal wall, extending vertically, divides the column into two zones between which the fluids do not flow, and a lower common part (c3).

Thus, compared with the alternative form illustrated in FIG. 3, the second column (C) comprises an upper common part (c1).

The invention claimed is:

1. A process for purification of a feedstock resulting from a process for depolymerization of styrene compounds, the process comprising at least the following steps:

(a) a separation step employing a distillation column fed at a bottom of the column with the feedstock and producing, at a top of the column, an extract rich in light compounds, at the bottom of the column a raffinate rich in heavy compounds and, by a sidestream withdrawal, a stream rich in styrene, the column having as sole heat supply the feedstock; and (b) a step of separation of the stream rich in styrene into at least a stream comprising predominantly ethylbenzene, a stream comprising predominantly styrene, and a stream of heavy compounds.

2. The purification process according to claim 1, wherein the feedstock comprises at most 10% by weight of ethylbenzene.

3. The purification process according to claim 1, wherein the feedstock comprises at least 10% by weight of compounds having a boiling point greater than styrene.

4. The purification process according to claim 1, wherein a temperature of the feedstock is greater than 300° C.

5. The purification process according to claim 1, wherein the process for the depolymerization of styrene compounds is a pyrolysis process and the feedstock resulting from a pyrolysis reactor directly feeds step (a) of the purification process, without intermediate cooling, heating or separation operations.

6. The purification process according to claim 1, wherein the distillation column of step (a) comprises from 5 to 20 theoretical stages.

7. The purification process according to claim 1, wherein a condenser of the distillation column of step (a) is operated at a temperature of between 30° C. and 50° C. and a vapor effluent from the condenser is subsequently cooled to a temperature of between −5° C. and 10° C.

8. The purification process according to claim 1, wherein a styrene polymerization inhibitor is fed at the top of the column in step (a) of the process.

9. The purification process according to claim 1, wherein the separation step (b) is performed in two successive separation sections:

(1) a first separation section which is fed with the stream rich in styrene resulting from step (a) and which separates the stream comprising predominantly ethylbenzene and a styrenic raffinate, carried out in a distillation column comprising from 60 to 100 theoretical stages, and operated at a pressure of less than or equal to 0.25 bara at the top of the column, and (2) a second separation section fed with the styrenic raffinate resulting from the first separation section and producing the stream comprising predominantly styrene and the stream of heavy compounds, carried out in a distillation column comprising from 40 to 100 theoretical stages, and operated at a pressure of less than or equal to 0.25 bara at the top of the column.

10. The purification process according to claim 1, wherein the separation step (b) is carried out in a divided wall distillation column fed with the stream rich in styrene resulting from step (a) and producing, at the top of the column, the stream comprising predominantly ethylbenzene, at the bottom of the column the stream of heavy compounds and, as the sidestream withdrawal, in a section separated from the feed section of the column by an internal wall, the stream comprising predominantly styrene, the divided wall distillation column comprising from 70 to 130 theoretical stages and being operated at a pressure of less than or equal to 0.25 bara at the top of the column.

11. The purification process according to claim 10, wherein the divided wall distillation column further comprises a lower common part comprising from 8 to 12 theoretical stages, of an upper common part comprising from 8 to 12 theoretical stages, and of a divided part comprising a remainder of the theoretical stages.

12. The purification process according to claim 10, wherein the divided wall distillation column further comprises a lower common part comprising from 2 to 12 theoretical stages and of a divided part comprising a remainder of the theoretical stages.

* * * * *